United States Patent
Purcell et al.

[19]

[11] Patent Number: 6,007,777
[45] Date of Patent: Dec. 28, 1999

[54] LIQUID SAMPLE CARBON ANALYZER

[75] Inventors: Michael W. Purcell, Mainville; Sheng Sheng Yang, Marshallville, both of Ohio; John Trifone Martin, Scotts Valley, Calif.; Richard R. Reckner, Cincinnati, Ohio; Jeffrey L. Harris, Hollister, Calif.

[73] Assignee: Tekmar Company, Cincinatti, Ohio

[21] Appl. No.: 09/072,943

[22] Filed: May 5, 1998

Related U.S. Application Data

[63] Continuation of application No. 08/746,885, Nov. 18, 1996, abandoned.

[51] Int. Cl.$^6$ .................................................. G01N 31/12
[52] U.S. Cl. ............................ 422/80; 422/68.1; 422/78; 422/103; 436/54; 436/145; 436/146; 436/181; 73/61.41; 73/863.21; 73/863.72; 73/864.34
[58] Field of Search ............................... 422/63, 67, 68.1, 422/78, 80, 81, 103; 436/52, 54, 145, 146, 175, 181; 73/61.41, 64.56, 863.21, 863.71, 863.72, 864.34

[56] References Cited

U.S. PATENT DOCUMENTS

| | | | |
|---|---|---|---|
| 2,549,258 | 4/1951 | Stover | 261/24 |
| 3,414,385 | 12/1968 | Beroza et al. | 422/99 |
| 3,499,670 | 3/1970 | Woody | 285/355 |
| 3,629,490 | 12/1971 | Keller | 358/521 |
| 3,695,642 | 10/1972 | DeWoody | 285/133.1 |
| 3,728,540 | 4/1973 | Todd et al. | 250/343 |
| 3,780,293 | 12/1973 | Flint | 250/339.03 |

(List continued on next page.)

FOREIGN PATENT DOCUMENTS

| | | |
|---|---|---|
| 0 684 471 A2 | 11/1995 | European Pat. Off. . |
| 41 38 916 A1 | 6/1992 | Germany . |
| 42 24 077 A1 | 2/1993 | Germany . |
| 08201274 | 8/1996 | Japan . |
| 08201376 | 8/1996 | Japan . |
| 09043224 | 2/1997 | Japan . |
| WO 91/13362 | 9/1991 | WIPO . |

OTHER PUBLICATIONS

"Filter Correlation Photometer", by W. Olsowski and V. Nestler, pp. 722–727, Rev. Sci. Instrum., 54(6), Jun. 1983.

"Introducing the ISCO EZ TOC Analyzer Accurate TOC Analysis Made Easy", prior art, Process Monitoring Division, 531 Westgate Blvd., Lincoln, NE 68528–1586, date unkn.

(List continued on next page.)

Primary Examiner—Maureen M. Wallenhorst
Attorney, Agent, or Firm—Westman, Champlin & Kelly, P.A.

[57] ABSTRACT

An analytical instrument measures carbon content of a liquid sample. The instrument includes a sample inlet, a reagent inlet, a rinsing solution inlet, a reaction chamber, a waste outlet and a syringe pump. A multiple port valve has a plurality of ports which are coupled to the sample inlet, the reagent inlet, the rinse solution inlet, the reaction chamber and the waste outlet. The valve also includes a primary port coupled to the syringe pump and selectively fluidically couplable to each of the remaining ports.

15 Claims, 9 Drawing Sheets

U.S. PATENT DOCUMENTS

| | | | |
|---|---|---|---|
| 3,832,548 | 8/1974 | Wallack | 250/343 |
| 3,861,809 | 1/1975 | Hall, Jr. | 356/418 |
| 3,955,930 | 5/1976 | Shapiro | 422/50 |
| 3,968,367 | 7/1976 | Berg | 250/339.13 |
| 3,973,915 | 8/1976 | Raffaele et al. | 422/50 |
| 4,057,499 | 11/1977 | Buono | 210/136 |
| 4,248,598 | 2/1981 | Blunck | 436/146 |
| 4,253,845 | 3/1981 | Smernoff | 436/11 |
| 4,256,461 | 3/1981 | Wallace et al. | 436/179 |
| 4,277,438 | 7/1981 | Eizak | 436/146 X |
| 4,288,229 | 9/1981 | Mar | 436/146 |
| 4,293,522 | 10/1981 | Winkler | 422/80 |
| 4,301,117 | 11/1981 | Smernoff | 422/99 |
| 4,342,912 | 8/1982 | Adamson | 250/339.14 |
| 4,344,918 | 8/1982 | Takahashi | 422/80 |
| 4,619,902 | 10/1986 | Bernard | 436/145 |
| 4,678,914 | 7/1987 | Melrose et al. | 250/343 |
| 4,692,621 | 9/1987 | Passaro et al. | 250/343 |
| 4,825,076 | 4/1989 | Shields | 250/343 |
| 4,850,697 | 7/1989 | Schoennauer et al. | 356/419 |
| 4,874,572 | 10/1989 | Nelson et al. | 376/256 |
| 4,913,821 | 4/1990 | Melcher et al. | 210/635 |
| 4,963,744 | 10/1990 | Matthys | 250/343 |
| 5,036,198 | 7/1991 | Spaeth | 250/343 |
| 5,075,550 | 12/1991 | Miller et al. | 250/338.5 |
| 5,097,130 | 3/1992 | Koashi et al. | 250/339.09 |
| 5,132,094 | 7/1992 | Godec et al. | 422/68.1 |
| 5,230,863 | 7/1993 | Salpeter | 422/67 |
| 5,241,178 | 8/1993 | Shields | 250/339.02 |
| 5,308,981 | 5/1994 | Perten | 250/339.11 |
| 5,340,542 | 8/1994 | Fabinski et al. | 422/82.05 |
| 5,413,763 | 5/1995 | Jeffers | 422/80 |
| 5,425,919 | 6/1995 | Inoue et al. | 422/67 |
| 5,443,991 | 8/1995 | Godec et al. | 436/145 |
| 5,518,608 | 5/1996 | Chubachi | 210/96.1 |
| 5,531,961 | 7/1996 | Wright et al. | 422/80 |

OTHER PUBLICATIONS

"A Measure of Purity", LabTOC Model 2100, Astro International Corporation, 100 Park Avenue, League City, TX 77473, prior art, date unknown.

"The Next Step in Automated TOC Analysis", 1992, Rosemount Analytical Inc. Dohrmann Division.

"Standard Test Method for Total, Organic, and Inorganic Carbon in High Purity Water by Ultraviolet (UV) or Persulfate Oxidation, or Both, and Infrared Detection", pp. 1–5, Technical Reprint, TR–021, Dohrmann Division, 1988.

"DC–190 High Temperature Total Organic Carbon Analyzer", Rosemount Analytical Inc. Dohrmann Division, 1992.

Selection of a TOC Analyzer, by Godfrey A. Crane, Dohrmann Division, Technical Reprint, TR–020, Jul. 1988, American Laboratory.

"Total Organic Carbon Analyzer", DC–80, Dohrmann Division, Rosemount Analytical Inc., 1994.

"TOC–5000 Total Organic Carbon Analyzer", Shimadzu Scientific Instruments, Inc. 7102 Riverwood Drive, Columbia, Maryland 21046, prior art, date unknown.

"On–Line Total Organic Carbon Monitoring for Ultrapure Water", 1991, Anatel Corporation.

"Automated. Affordable. TOC Analysis.", 1990, Astro International Corporation, 100 Park Avenue, League City, Texas 77573.

"700 Total Organic Carbon Analyzer", 1988, OI Corporation, Graham Rd. at Wellborn Rd., P.O. Box 2980, College Station, Texas 77841–2980.

"A New Instrument For The Determination Of Organic Carbon Levels In Water", Anatoc Total Organic Carbon Analyzer, 1993, SGE International Pty Ltd, Australia.

"Model ASI–5000 Automatic Sample Injector", Shimadzu Scientific Instruments, Inc., 1993.

"The Model SSM–5000 Combines With The TOC–5000 or TOC–5050 to Form A Solid Sample TOC Analysis System.", Shimadzu Scientific Instruments, Inc., 1993.

"New Technology For TOC Analysis In Water", by Richard Godec, Kevin O'Neill, and Richard Hutte, Ph.D., 1992, Sievers Instruments Inc., pp. 17–22.

"Total Organic Carbon Analyzer Sievers 800", Sievers Instruments, Inc. 2500 Central Ave., Suite H1, Boulder, CO 80301, 1992.

Total Organic Carbon Analyzer TOC–5000 On–Line Measurement System, 1993, Shimadzu Scientific Instruments, Inc.

"Labtoc Laboratory TOC Water Analysis System", 1993, Pollution & Process Monitoring.

"Carbon & Sulfor Analysis", UIC Inc., P.O. Box 863, Joliet, Illinois 60434–0863, prior art, date unknown.

"Skalar SK[12] Analyser A New Concept For Fully Automated TOC/DOC Analysis", prior art, date unknown.

"Recent Advances In The Measurement Of Total Organic Carbon In Water", by Richard S. Hutte, Richard Godec, Kevin O'Neill, Sievers Instruments, Inc., prior art, date unknown.

"Model ESU–1 External Scrubber Unit", Shimadzu, prior art, date unknown.

"TOC–500 Total Organic Carbon Analyzer", Shimadzu, prior art, date unknown.

"TOC–5050 Total Organic Carbon Analyzer", Shimadzu Scientific Instruments, Inc., prior art, date unknown.

"Ionics Advanced Chemical Analysis Technology TOC POC TC Laboratory Analyzers", prior art, Ionics, Incorporated, Instrument Division, 65 Grove Street, Watertown, MA 02172, date unknown.

"The Plus That Redefines The Possible In High Temperature TOC", HT 680+, date unkn prior art, Astro International Corporation, 100 Park Avenue, League City, Texas 77573.

LIQUID SAMPLE CARBON ANALYZER

CROSS REFERENCE TO RELATED APPLICATIONS

This application is a continuation application of application Ser. No. 08/746,885, filed Nov. 18, 1996, now abandoned, entitled "LIQUID SAMPLE CARBON ANALYZER" and assigned to the same assignee as the present application.

BACKGROUND OF THE INVENTION

The present invention relates generally to analyzers that measure the carbon content of a sample. More specifically, the invention relates to chemical analyzers that can measure the total organic carbon ("TOC"), the inorganic carbon ("IC"), or the total carbon ("TC"; TC=TOC+IC) content of a sample or specimen.

The measurement of carbon content in liquids such as drinking water, treated or untreated wastewater, and ultrapure water for pharmaceutical or clean room applications is a routine way to assess the purity of the liquid sample. Solid or semi-solid specimens such as soils, clays, or sediments can likewise be measured for carbon content using known analyzer accessories.

Syringe pumps have been used in prior art dissolved carbon analyzers, but generally only in those that use a combustion-type reactor to convert dissolved organic carbon to gaseous $CO_2$. Such combustion reactors can accept only relatively small volumes (less than about 2.5 ml) of the sample of interest; therefore, the syringe pumps used in the prior art have had low volume (2.5 ml) capacities. Prior art analyzers that use the known UV or UV/persulfate or heated/persulfate techniques have generally used a peristaltic pump in series with a fixed volume sample loop to dispense the sample of interest. Ultraviolet ("UV") reaction chambers can accept larger volumes (up to about 25 ml) of the sample of interest, permitting measurement of lower concentrations of dissolved carbon in the sample. An object of the invention is to combine the flexibility of a syringe pump for dispensing sample with the high sensitivity UV reaction technique.

Prior art dissolved carbon analyzers, particularly those utilizing the known UV, UV/persulfate, or heated/persulfate oxidation techniques, have used a multiplicity of valves, connections, and tubing connected together in a complicated arrangement that increases the likelihood of leaks or contamination and makes diagnosis of instrument problems very difficult. Therefore another object of the invention is to simplify the flow path of a dissolved carbon analyzer by incorporation of a syringe pump and multiple-port valve.

Known dissolved carbon analyzers use flexible tubes to carry fluids between valves, connections, and other components of the analyzer. When servicing such analyzers, it becomes very difficult to identify and track any particular tube or series of tubes because the tubes are grouped together at various locations and all have the same appearance. Thus another object of the invention is to facilitate the identification or tracking of tubes in a dissolved carbon analyzer.

Other objects of the invention will become apparent from the detailed description of the invention and the accompanying drawings.

BRIEF SUMMARY OF THE INVENTION

An analytical instrument measures carbon content of a liquid sample. The instrument includes a sample inlet, a reagent inlet, a rinsing solution inlet, a reaction chamber, a waste outlet and a syringe pump. A multiple port valve has a plurality of ports which are coupled to the sample inlet, the reagent inlet, the rinse solution inlet, the reaction chamber and the waste outlet. The valve also includes a primary port coupled to the syringe pump and selectively fluidically couplable to each of the remaining ports.

According to one preferred feature of the present invention, the analytical instrument has a plurality of tubes which carry fluids between various components of the analytical instrument. At least one of the plurality of tubes has an appearance which is different from that of the rest of the plurality of tubes.

According to another preferred feature of the present invention, the reaction chamber is a UV reaction chamber which includes a vessel and a UV lamp is disposed in the vessel. The UV lamp has a spiral configuration.

For convenience, items in the figures having the same reference symbol are the same or serve the same or a similar function.

DETAILED DESCRIPTION OF THE PREFERRED EMBODIMENTS

Figure 1:
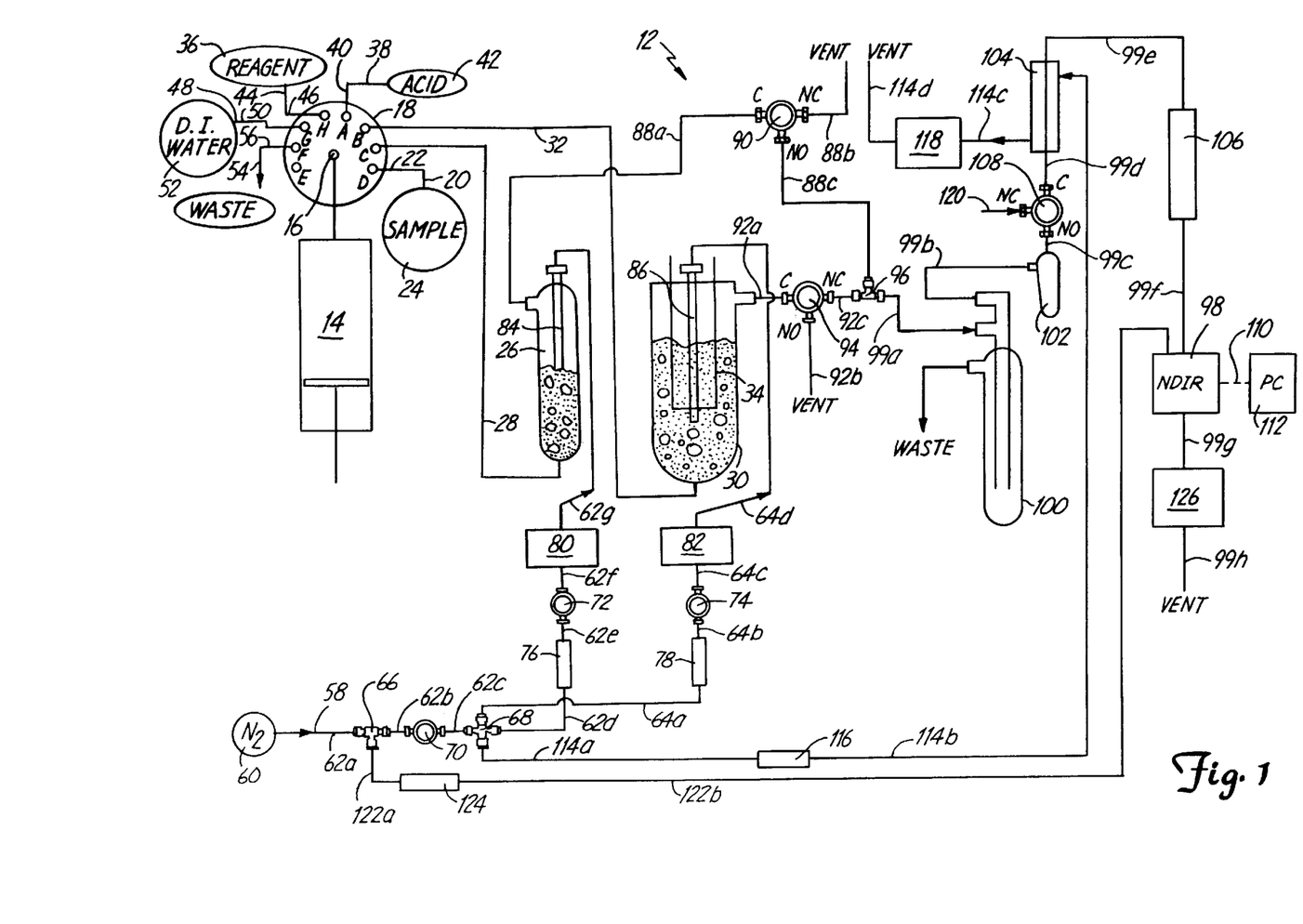
FIG. 1 shows a preferred flow path of a dissolved carbon analyzer.

FIG. 1 depicts a preferred dissolved carbon analyzer 12 according to the invention. A motor-driven syringe pump 14 connects to a primary port 16 of a multiple port valve 18. Valve 18 also includes ports A,B,C,D,E,F,G,H, and is operable to fluidically couple primary port 16 to any one of the other ports. When primary port 16 couples to one of ports A–H, the remainder of ports A–H are isolated from each other and from primary port 16. Valve 18 can be actuated pneumatically or preferably electrically, with both clockwise and counterclockwise action. Valve 18 is preferably an 8-port valve as shown and available from Kloehn Co. Ltd., Las Vegas, Nev. under part No. 50300-0.9.

As discussed above syringe pumps have been used for sample delivery in prior art dissolved carbon analyzers but not in UV-reaction systems, and not where a high volume sample was required for trace level analysis. Analyzer 12 uses a UV-type reactor and a syringe pump 14 that has a high volume capacity of at least about 10 ml and preferably about 25 ml.

Port D of valve 18 couples to a sample inlet 20 over a line 22. The sample inlet 20 receives a sample of interest 24 to be analyzed, which sample can be provided individually or in an autosampler that holds many other samples of interest.

Port C couples to a sparging chamber 26 over a line 28. In sparging chamber 26, dissolved IC and purgeable organic compounds ("POC"s) can be removed from the sample by adding acid to the sample and sparging the resulting mixture.

Port B couples to a UV reaction chamber 30 over a line 32. In chamber 30, UV light from a UV lamp 34 converts organic carbon in the sample into $CO_2$ gas. A reagent 36 is preferably present in the chamber 30 with the sample to accelerate the reaction.

Port A couples to an acid inlet 38 over a line 40. The acid inlet receives acid from a reservoir of acid 42, preferably a 25% solution of phosphoric acid ($H_3PO_4$).

Port H couples to a reagent inlet 44 over a line 46. The reagent inlet receives reagent from a reservoir of reagent 36, preferably 10% sodium persulfate ($Na_2S_2O_8$), but 2% or 3% potassium persulfate ($K_2S_2O_8$) can also be used. Reagent 36 preferably also includes about 5% phosphoric acid. The persulfate/acid mixture of reagent 36 is used primarily in the UV reaction chamber 30, whereas the acid 42 by itself is used primarily in the sparging chamber 26. One purpose for this separation is to maintain good sparging efficiency in both chambers 26 and 30. Unlike the UV reaction chamber, the sparging chamber has no UV source to break down persulfate. Residual persulfate can cause a precipitate to slowly build up on surfaces in the chamber, including the glass frit used as a disperser. Such build-up can clog portions of the frit, gradually degrading sparging efficiency.

Port G couples to a rinse solution inlet 48 over a line 50. The rinse solution inlet 48 receives a rinse solution such as deionized water 52.

Port F couples to a waste outlet 54 over a line 56. Port E as shown is unused.

With syringe pump 14 and multiport valve 18 oriented vertically as shown, it is possible for minute portions (microliter levels) of liquid residue in upper ports A,H,B,G to fall into syringe pump 14, causing contamination. Therefore, since acid 42, reagent 36, and rinse solution 52 have low and consistent carbon concentrations which are measurable, those liquids preferably couple to adjacent upper ports G,H,A. Sample 24 on the other hand connects to downward-facing port D to avoid such contamination. Chambers 26,30 as shown preferably connect to adjacent ports B,C between sample port D and ports A,H,G used for liquids 42,36,52. This arrangement, coupled with the bidirectional capability of valve 18, minimizes valve movement during operating procedures described below, thereby also minimizing contamination.

Analyzer 12 also includes a carrier gas inlet 58 which receives a pressure regulated carrier gas source 60 such as nitrogen or what is known in the art as ultra-zero air. Lines 62a–g,64a–d, T-connection 66, cross-connection 68, electrically controlled on/off valves 70,72,74, flow restrictors 76,78, and optional flowmeters 80,82 are connected as shown to permit carrier gas to be routed to a sparge tube 84 of sparging chamber 26 and to a sparge tube 86 of UV reaction chamber 30. Sparge tubes 84 and 86 preferably are each made of glass and as noted above have a standard glass frit (not shown in FIG. 1) affixed at the bottom thereof as is known in the art to disperse the carrier gas evenly through the sample and avoid channeling.

A line 88a carries gasses away from sparging chamber 26 to an electrically controlled 3-port valve 90. Likewise, a line 92a carries gasses away from UV chamber 30 to a valve 94 which is identical to valve 90. In an "off" state, valves 90,94 connect a common "C" port to a normally open "NO" port while a normally closed "NC" port is isolated. In an "on" state, the C port connects to the NC port and the NO port is isolated. Gas from sparging chamber 26 can thus be vented via a line 88b or sent to a $CO_2$ detector via a line 88c, depending on the state of valve 90. In like manner gas from UV chamber 30 can be vented over a line 92b or sent to a $CO_2$ detector over a line 92c. Lines 88c,92c meet at a T-connection 96. Gas flows from T-connection 96 to a non-ispersive infrared ("NDIR") or other suitable $CO_2$ detector 98 having a linearized output via lines 99a–f, a gas/liquid separator 100, a mist trap 102, a permeation tube 104, a scrubber 106, and a valve 108 as shown. The gas/liquid separator 100, mist trap 102, and permeation tube 104 are standard components and function to remove water vapor, which can interfere with the $CO_2$ measurement, from the gas stream. Scrubber 106 preferably comprises a U-shaped glass tube having a quantity of tin beads sandwiched between Pyrex brand wool plugs in one arm of the "U" and a quantity of copper beads sandwiched between like plugs in the other arm of the "U". The scrubber 106 removes chlorine, which can also interfere with the $CO_2$ measurement and also harm the detector 98, from the gas stream by reaction with the copper and tin beads. Discoloration of the copper beads, which are disposed upstream of the tin beads, provides an indication that the scrubber 106 should be replaced. Detector 98 provides a linearized signal over a line 110 indicative of the amount of $CO_2$ in the gas stream to a computer 112 communicating with analyzer 12. The computer, or a dedicated controller resident in the analyzer 12, also controls the valves 18,70,72,74,90,94,108 and syringe pump 14 to execute the various methods of operation.

Carrier gas is also supplied through lines 114a,b and flow restrictor 116 to permeation tube 104, exiting via lines 114c,d to vent. Block 118 represents one or more of the reservoirs for rinse solution 52, reagent 36, and acid 42. By bubbling clean carrier gas through such reservoirs, carbon contamination can be minimized.

Valve 108 is identical to valves 90,94 and is optional. A line 120 can connect to other $CO_2$ generating devices such as a solid sample preparation device (not shown) and routes the gas stream to be analyzed to detector 98 when valve 108 is on.

Carrier gas is also supplied to a reference channel of $CO_2$ detector 98 over lines 122a,b and a flow restrictor 124. Flow restrictors 76,78,116,124 are preferably regulated by input carrier gas pressure up to 200, 200, 100, and 20 ml/minute respectively. The sample gas stream exits $CO_2$ detector 98 by a line 99g, an optional flowmeter 126, and a line 99h to vent.

The flowpath of analyzer 12 in FIG. 1 is greatly simplified compared to prior dissolved carbon analyzers, particularly UV-reactor type analyzers, by making effective use of syringe pump 14 and multiple port valve 18. The single valve 18, by virtue of its multiplicity of ports selectively coupleable to the primary port, connects the syringe pump to each of seven different inlets, chambers, or outlets. No other valves are required in the liquid handling path.

Figure 2:
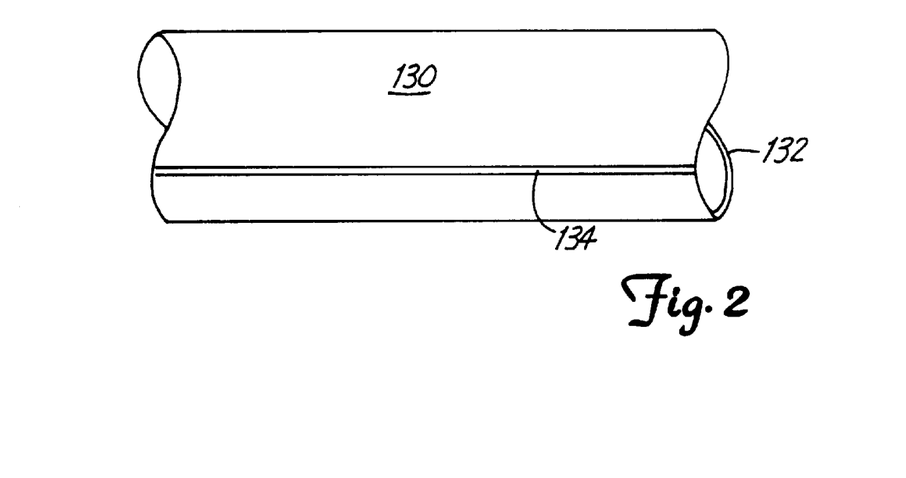
FIG. 2 is cutaway view of a length of tubing used in a preferred analyzer.

The components shown in FIG. 1 are preferably arranged in or on an analyzer cabinet. Syringe pump 14, multiple port valve 18, sparging chamber 26, UV chamber 30, gas/liquid separator 100, mist trap 102, and scrubber 106 are preferably mounted on a front panel of the analyzer cabinet for ease of viewing to verify operation. Valves 70,72,74,90,94,108, flow restrictors 76,78,116,124, T-connections 66,96, and cross-connection 68 are preferably mounted elsewhere in the analyzer cabinet. Each of the lines that interconnect the various components of the analyzer (i.e., lines 56,50,46,40, 32,28,22,62a–g,64a–d,88a–c,92a–c,99a–h,114a–d,122a–b) is a length of flexible tube preferably made of Teflon brand polymer and typically of small size (0.125 or 0.0625 inch O.D.). Many such tubes are bundled together at different locations in the cabinet, making it difficult for a user or servicer of the analyzer to readily trace the flow path as is sometimes desirable. To alleviate this problem analyzer 12 preferably uses different types of tubes for interconnections. The different types of tubes have appearances that differ from one another. The tubes are preferably color-coded to signify their function in the flow path. For example, blue tubes can be used for lines that carry fluids exclusively to or from the UV chamber 30, and red tubes can be used for lines that carry fluids exclusively to or from the sparging chamber 26. Yellow tubes can then be used for all other lines. Although solid opaque colored tubing can be used, it is preferred to use transparent or at least translucent tubing that has a colored stripe or other colored or even monochrome indicia that makes at least one tube distinguishable from other tubes. Transparent tubes permit an observer to detect the presence of a liquid or a foreign object in the tube. FIG. 2 shows a section of a preferred tube 130. The tube wall 132 is transparent. A colored stripe 134 extends along the length of the tube 130. The following table shows one possible color scheme:

| Color | Function | Lines |
|---|---|---|
| Blue | To/from UV chamber | 22,46,32,64c–d,92a,92c |
| Red | To/from sparging chamber | 28,40,62f–g,88a,88c |
| Green | To/from moisture control elements | 99a–h |
| Yellow | Other carrier gas | 62a–e,64a–b,114a–d,122a–b |
| Black | To waste or vent | 56,88b,92b |
| Clear | Rinse water | 50 |

Figure 3A:
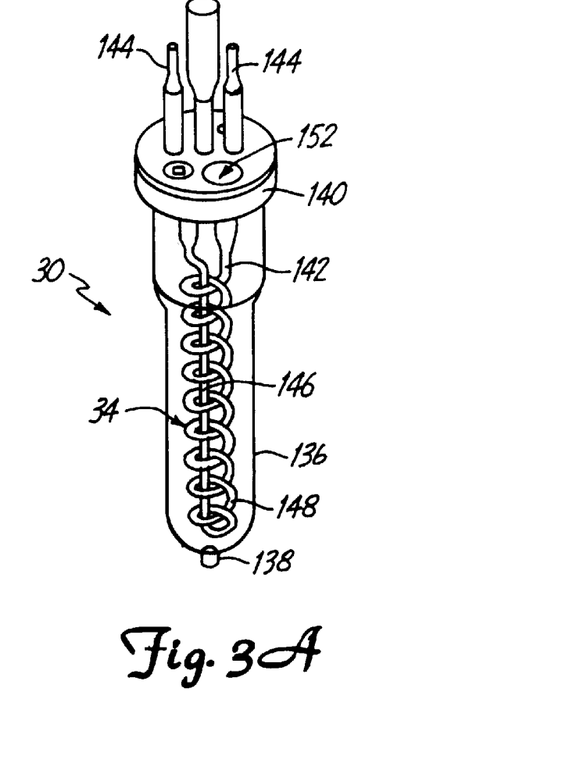
FIGS. 3a and 3b are perspective views of portions of a preferred UV reaction chamber useable in the analyzer of FIG. 1.
Figure 3B:
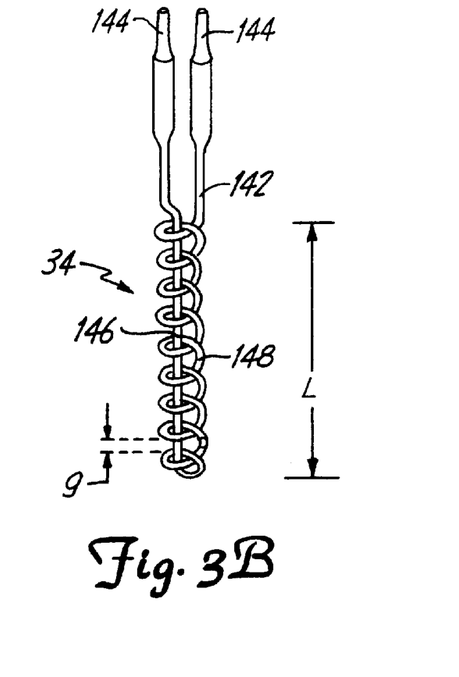

Turning now to FIGS. 3a and 3b, we see some details of the preferred UV reaction chamber 30. Chamber 30 includes a vessel 136 having a drain/fill port 138 at the bottom thereof and sealed by a threaded cap 140 at the top. The vessel 136 is preferably made of Pyrex brand glass or other suitable UV-absorbing material. Disposed in the vessel is a mercury vapor UV lamp 34 comprising a hollow silica tube 142 sealed at its ends. Analyzer 12 includes a high voltage power supply (not shown) that couples to electrical terminals 144 to continuously excite UV lamp 34. Except for widened stems at the terminals 144, silica tube 142 has a uniform diameter d of about 4 millimeters (mm) including a straight portion 146 around which is wrapped a spiral portion 148. Spiral portion 148 has an overall length L of about 55 mm and preferably has about 8 tightly wound coils of outer diameter 22 mm. A gap g between adjacent coils is about 2 to 3 mm, preferably no greater than the silica tube diameter d. Coiled portion 148 contacts the bottom of vessel 136 and is spaced apart from the vessel 136 side wall by a small gap of about 3 mm. The configuration of the tightly coiled portion 148 in vessel 136 ensures that a liquid injected into UV chamber 30 through drain/fill port 138 will be adequately exposed to UV radiation, for liquid volumes as large as 30 ml and as small as 5 ml. Two of the coils are immersed for a 5 ml liquid and all 8 coils are immersed for a 20 ml liquid.

Figure 4:
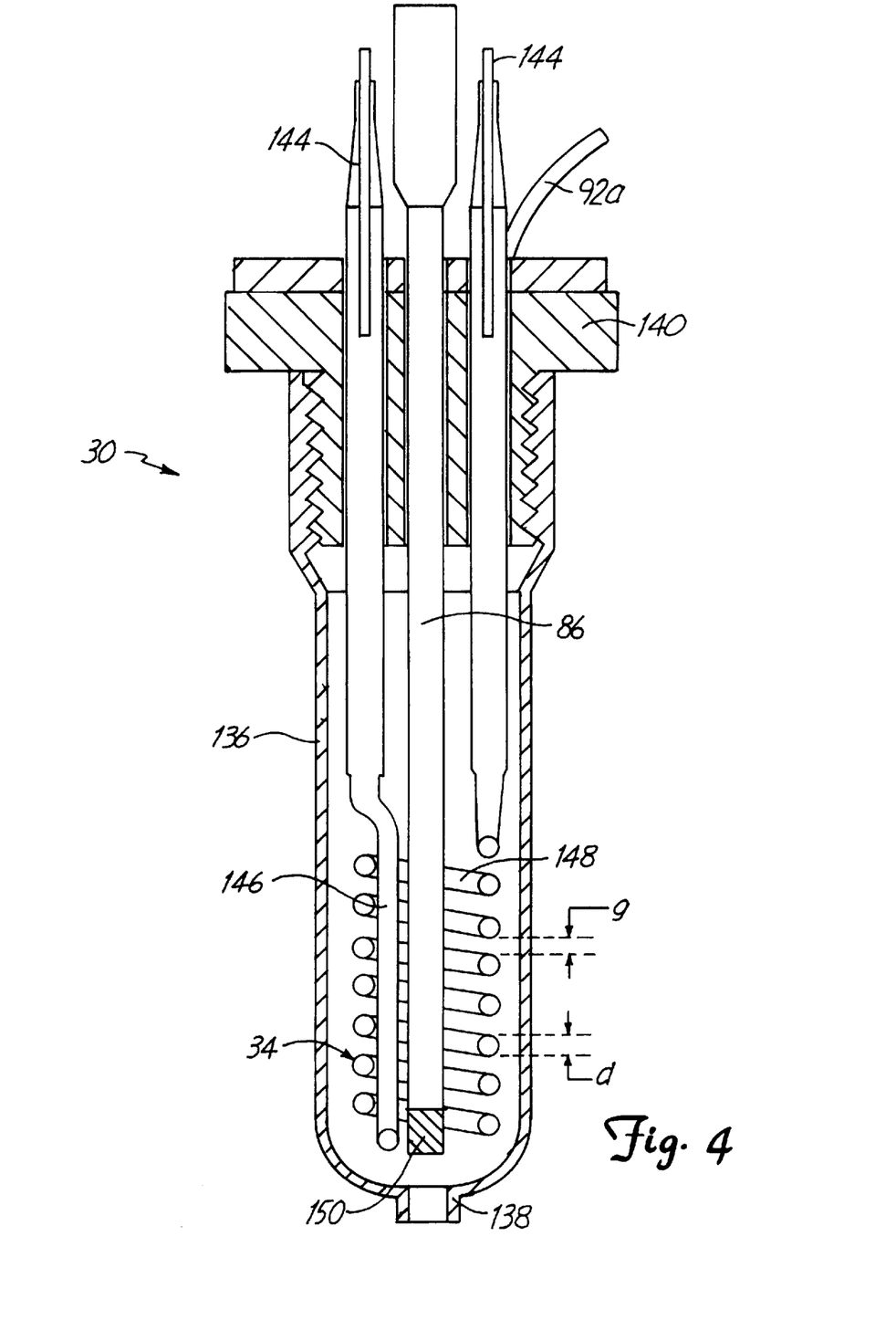
FIG. 4 is a sectional view of a preferred UV reaction chamber useable in the analyzer of FIG. 1.

As is more clearly seen in the sectional view of FIG. 4, the straight portion 146 is preferably decentered within coiled portion 148 to permit the sparge tube 86 to extend down through coiled portion 148 to the bottom of vessel 136. A glass frit 150 disperses carrier gas throughout the liquid in vessel 136. The carrier gas along with any $CO_2$ gas produced by UV-assisted reaction of dissolved carbon in the sample with persulfate are released from UV chamber 30 through a vent port 152 (FIG. 3a) and sent via line 92a to vent or to the $CO_2$ detector.

Figure 5:
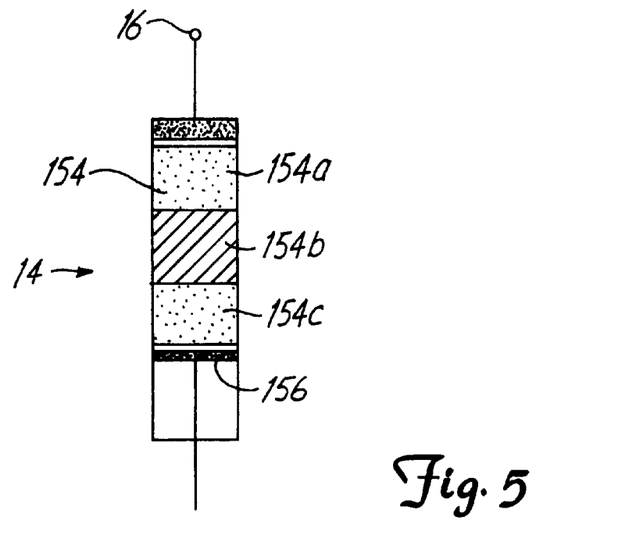
FIG. 5 is a schematic view of a loaded syringe pump that illustrates a preferred sample delivery technique.

An advantage of using a syringe pump rather than a sample loop for sample delivery is that any desired sample volume up to the capacity of the syringe can be obtained and delivered to the reaction chamber. However, it is possible for small bubbles to form in an aspirated sample inside the syringe pump. Such bubbles can cause the volume of a delivered sample to be erroneously low, leading to errors in the calculated concentration of dissolved carbon in the sample. The effect is most pronounced for low sample volumes. To avoid such errors, analyzer 12 uses a sample delivery technique explained with the aid of FIG. 5. In FIG. 5, a liquid 154 has been drawn into the syringe pump 14 through one of the ports of multiport valve 18 (see also FIG. 1). The liquid 154 can be the sample 24, or rinse solution 52, or acid 42, or reagent 36, or a mixture of same obtained from sparging chamber 26 or UV chamber 30. It has been found that bubbles can collect not only at the top of the liquid 154 but also at the bottom along the surface of the piston 156. The delivery technique involves loading a larger volume of sample (preferably 2 ml more) than the desired delivery volume. Then, after cycling multiport valve 18 to connect primary port 16 to the waste outlet 54, a top portion 154a (preferably 1 ml) of liquid 154 is sent to waste. After that the multiport valve 18 is cycled to a desired destination such as sparging chamber 26 or UV chamber 30, and a middle portion 154b of liquid 154, having the desired delivery volume, is sent to the destination. Finally, the multiport valve 18 connects primary port 16 back to waste outlet 54 and discharges a remaining bottom portion 154c (preferably 1 ml) of liquid 154 to waste.

Cleaning Procedure

The dissolved carbon analyzer 12 also preferably makes use of a unique procedure for cleaning the sparging chamber 26, the UV chamber 30, and interconnecting lines. The procedure removes from the flow path residual carbon left over from a previous sample or from other sources after a prolonged period of nonuse. The procedure also preferably provides an indication that confirms the cleaning performance.

Figure 6:
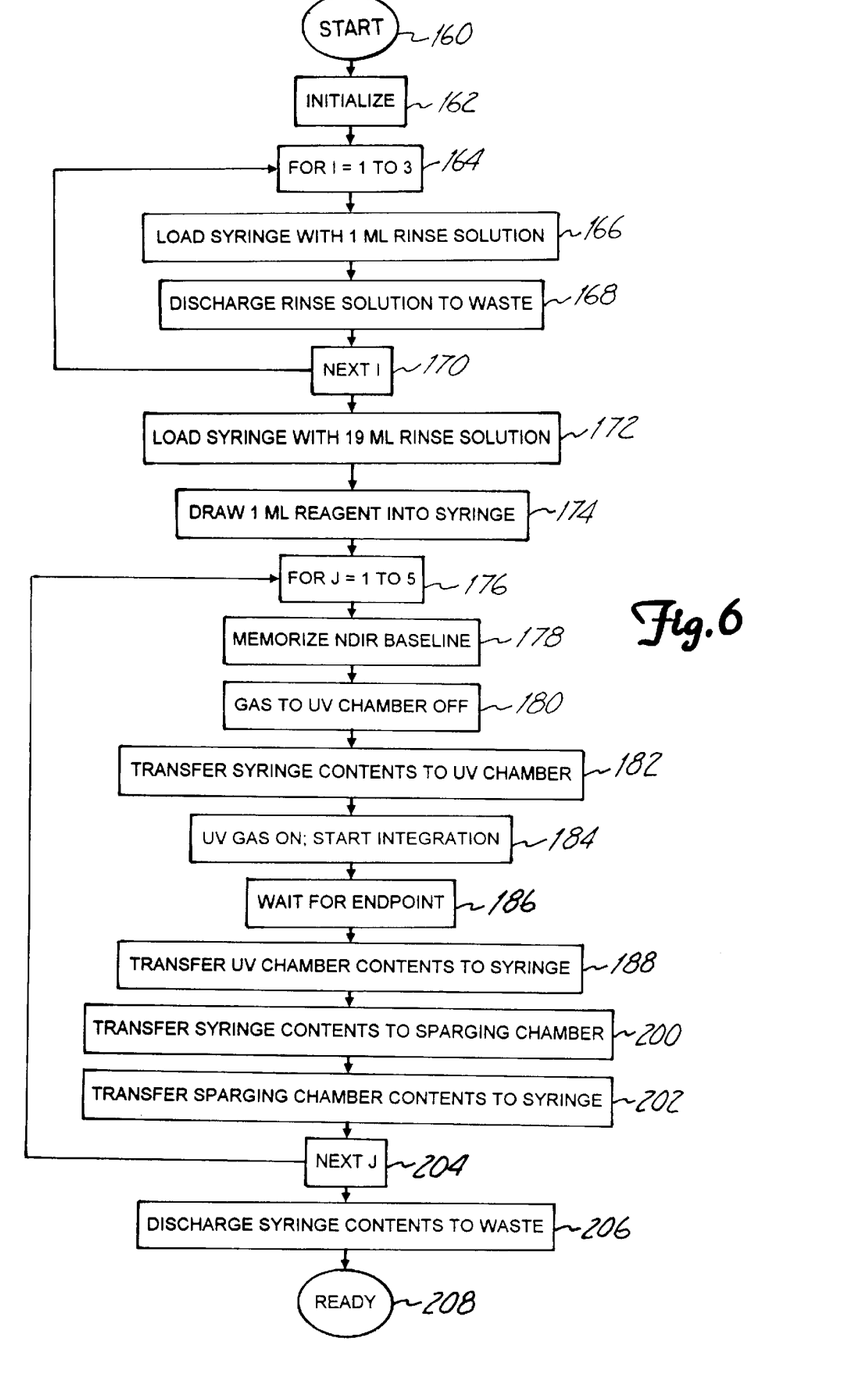
FIG. 6 is a flow chart showing a preferred cleaning operation to reduce carbon contaminants in a dissolved carbon analyzer.

FIG. 6 shows a flow diagram of the cleaning procedure. After a start command at 160, which is preferably given whenever analyzer 12 is initially powered-up, operation flows to an initialize block 162. There, valves 72,74,90,94 are all set to "on" so that carrier gas flows through sparging chamber 26 to vent, and carrier gas flows through UV chamber 30 to $CO_2$ detector 98. (Unless otherwise specified, valve 70 and UV lamp 34 are always on and valve 108, if present, is always off.) After initialization, operation proceeds to a loop indicated by a counter "i" in blocks 164,170 and shown to be executed 3 times. At block 166 multiple port valve 18 cycles to port G and syringe pump 14 aspirates 1 ml of rinse solution 52. Valve 18 then at block 168 cycles to port F and syringe pump 14 discharges the collected rinse solution to waste. After 3 loops, operation proceeds to block 172, where valve 18 cycles again to port G and syringe pump 14 aspirates a larger volume, preferably about 19 ml, of rinse solution. At block 174, valve 18 cycles to port H and syringe pump 14 draws about 1 ml of reagent 36 for a combined 20 ml of liquid resident in the syringe.

Operation then proceeds to a loop indicated by a counter "j" in blocks 176,204 and shown to be executed 5 times. The "i" or "j" loops can of course be executed any other desired number of times. At block 178, the computer 112 monitors the output of $CO_2$ detector 98 and stores the output as a baseline reference value. Valve 74 is turned off at block 180, shutting off carrier gas flow to UV chamber 30. Turning off the carrier gas flow just prior to loading the UV chamber with a liquid sample and then turning the carrier gas flow back on after loading is complete results in a well defined single-peaked response at $CO_2$ detector 98. The valve 18 cycles to port B and all 20 ml of syringe contents are pumped to UV chamber 30 at block 182. During this step any contaminants in line 32 are picked up and carried to UV chamber 30. Also, the UV light in cooperation with the persulfate in the reagent 36 immediately begin breaking down organic carbon into $CO_2$ gas. Valve 74 is turned on at block 184, causing carrier gas to sweep any $CO_2$ in UV chamber 30 to $CO_2$ detector 98. Computer 112 immediately begins to integrate the $CO_2$ detector output, which will typically rise from its baseline value to a peak value and then return to its baseline value. Since carbon is broken down in UV chamber 30 over an extended period of time, the time integration of the $CO_2$ detector signal rather than its peak value is most representative of carbon content of the liquid. Integration stops when an endpoint condition is met in block 186. The endpoint condition is satisfied when the $CO_2$ detector output falls to within a programmed value of the baseline value, or when a programmed maximum integration time limit has elapsed since the onset of integration in block 184, whichever comes first. When operation leaves block 186, computer 112 can subtract the baseline value times the actual integration time from the integrated detector output to calculate a value representative of carbon content in the liquid, which representative value is displayed on computer 112.

At block 188, syringe pump 14 aspirates all of the liquid in UV chamber 30. Multiport valve 18 then cycles to port C and the liquid is injected into sparging chamber 26 at block 200 through line 28. Immediately thereafter, syringe pump 14 draws the liquid back out of the sparging chamber at block 202. The sequence of operations from block 178 to block 202 are then repeated until a total of 5 or another programmed number of cycles are complete. With each subsequent cycle of the "j" loop, the 20 ml volume of liquid collected at the end of block 174 has progressively less carbon content, as can be confirmed by observing the representative values displayed by computer 112. By transferring the liquid repeatedly between the UV chamber, syringe pump, and sparging chamber via the valve 18 and lines 28,32, substantially the entire liquid flow path is also cleaned to the same degree. After the required cycles of the "j" loop are complete, operation passes to block 206 where the multiport valve cycles to port F and syringe pump 14 discharges the 20 ml liquid to waste. Finally, operation proceeds to an instrument ready condition at block 208.

Figure 7:
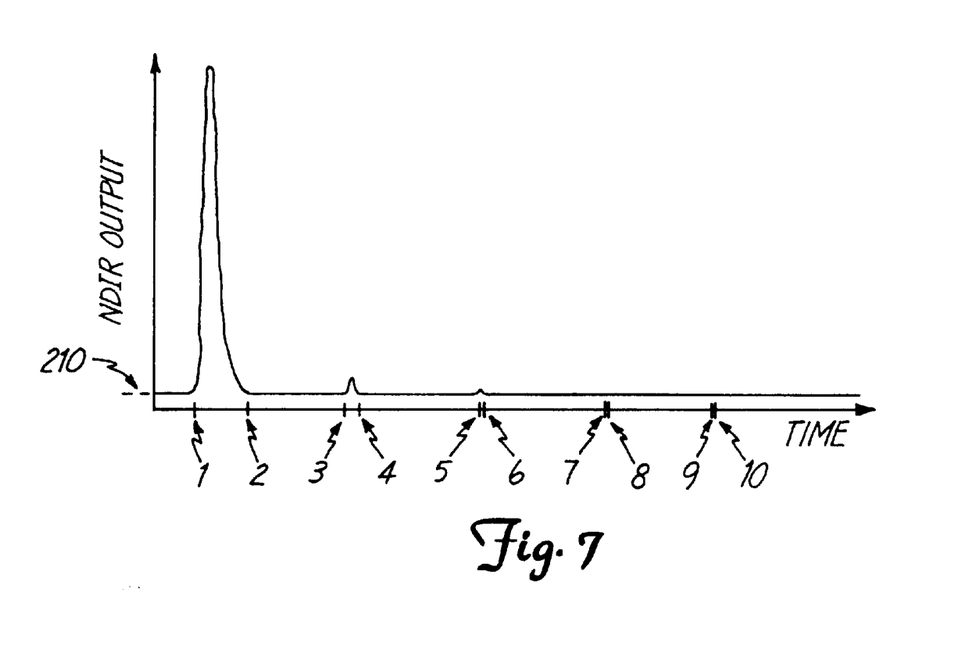
FIG. 7 is a graph of a $CO_2$ detector output associated with the cleaning operation of FIG. 6.

FIG. 7 shows a hypothetical output of a linearized NDIR $CO_2$ detector 98 as a function of time during the cleaning procedure of FIG. 6. The baseline detector output 210 is shown exaggerated. Time values 1,3,5,7,9 correspond to block 184 for each of the five "j" loops and time values 2,4,6,8,10 correspond to the completion of block 186 when the endpoint condition is met for each of the "j" loops. Both the peak value and the area of the well defined $CO_2$ peaks can be seen to decrease rapidly with each successive "j" loop cycle.

TOC (by NPOC) Procedure

It is known that the TOC of many samples can be ascertained by measuring the non-purgeable organic carbon ("NPOC") content of such samples. First, acid is added to the sample and the resulting mixture is sparged, removing IC and purgeable organic carbon ("POC") from the sample. Next a persulfate solution is added to the mixture and the resulting new mixture is exposed to UV radiation. NPOC, the only remaining carbon in the sample, is converted to $CO_2$ which is measured by the $CO_2$ detector.

Figure 8:
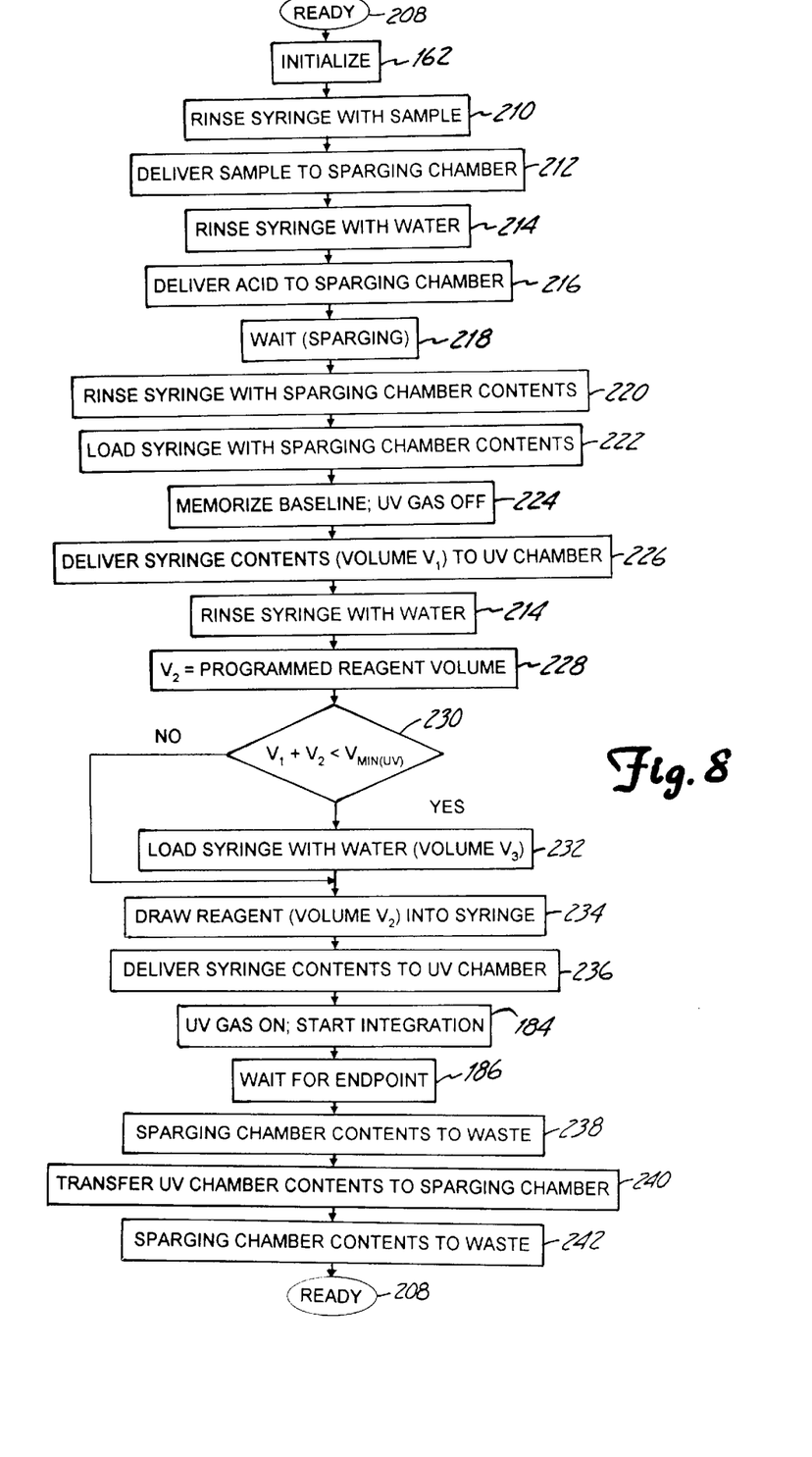
FIG. 8 is a flow chart of a preferred method of measuring TOC.

FIG. 8 shows the preferred method employed by analyzer 12 to carry out the TOC/NPOC analysis. Preferably, the method is carried out by a microprocessor-based controller included in analyzer 12. Blocks that perform the same function as previously described blocks have the same reference numeral. After the initialization block 162, block 210 executes a triple rinse sequence similar to blocks 164–170 of FIG. 6 except that 1 ml of sample 24 rather then 1 ml of rinse solution is loaded and discharged to waste. In block 212 a programmed volume of sample 24 is delivered to sparging chamber 26 using the delivery method described by FIG. 5. The syringe is rinsed with water or other rinse solution 52 at block 214 using the procedure of block 210, and at block 216 a volume of acid is injected through line 28 to sparging chamber 26. The sequence of blocks 212 and 216 is preferred over other alternatives, such as loading both sample and acid into the syringe and then delivering the resulting mixture to the sparging chamber, because it permits larger volumes of sample to be delivered to the sparging chamber, and because the acid delivery step of block 216 flushes any sample resident in line 28 into the sparging chamber, ensuring complete processing of the programmed volume of sample. Sparging of the acid/sample mixture continues for a programmed wait period at block 218. Any $CO_2$ or other carbon species exiting sparging chamber 26 are released to vent through line 88b. A triple rinse procedure similar to that of block 214 is carried out at block 220, with the acid/sample mixture being sequentially loaded and sent to waste. At block 222 the acid/sample mixture is aspirated into the syringe. Block 224 carries out previously described blocks 178,180 in sequence. A volume $V_1$ of syringe contents (acid/sample mixture) are then delivered to the UV chamber at block 226 using the FIG. 5 preferred delivery method. After another rinse block 214 control moves to a decision block 230. (Block 228 is inserted in FIG. 8 to define $V_2$ as a previously programmed or defined volume of reagent to be mixed with the sample/acid volume $V_1$.)

Before charging the syringe with reagent, decision block 230 checks to see if the combined acid/sample volume $V_1$ and the programmed reagent volume $V_2$ will achieve a minimum recommended liquid volume for UV chamber 30, called $V_{min(UV)}$. $V_{min(UV)}$ is selected to ensure the liquid adequately covers a substantial portion of the UV lamp and sparge tube 86. Only if the calculated volume is less than $V_{min(UV)}$, the syringe is loaded at block 232 with a volume $V_3$ of rinse solution that will bring the total liquid volume in the UV chamber to $V_{min(UV)}$. I.e., $V_3=V_{min(UV)}-(V_1+V_2)$. At block 234 the desired reagent volume is added to the syringe. The reagent volume $V_2$ (and the volume $V_3$ of rinse solution loaded in block 232, if any) is delivered to the UV chamber at block 236. This step flushes any sample resident in line 32 into UV chamber 30 to again ensure complete processing of the sample. The UV radiation from lamp 34 immediately begins converting organic carbon in the sample to $CO_2$ gas. Blocks 184,186 described previously are then executed. After the endpoint condition is satisfied any remaining sparging chamber contents are sent to waste at block 238. The sparging chamber is then rinsed by transferring the now carbon-free contents of the UV chamber to the sparging chamber at block 238 (a combination of prior blocks 188 and 200) and then expelling such contents to waste at block 242 (a combination of blocks 202 and 206). The analyzer 12 then returns to its instrument ready state 208.

Figure 9:
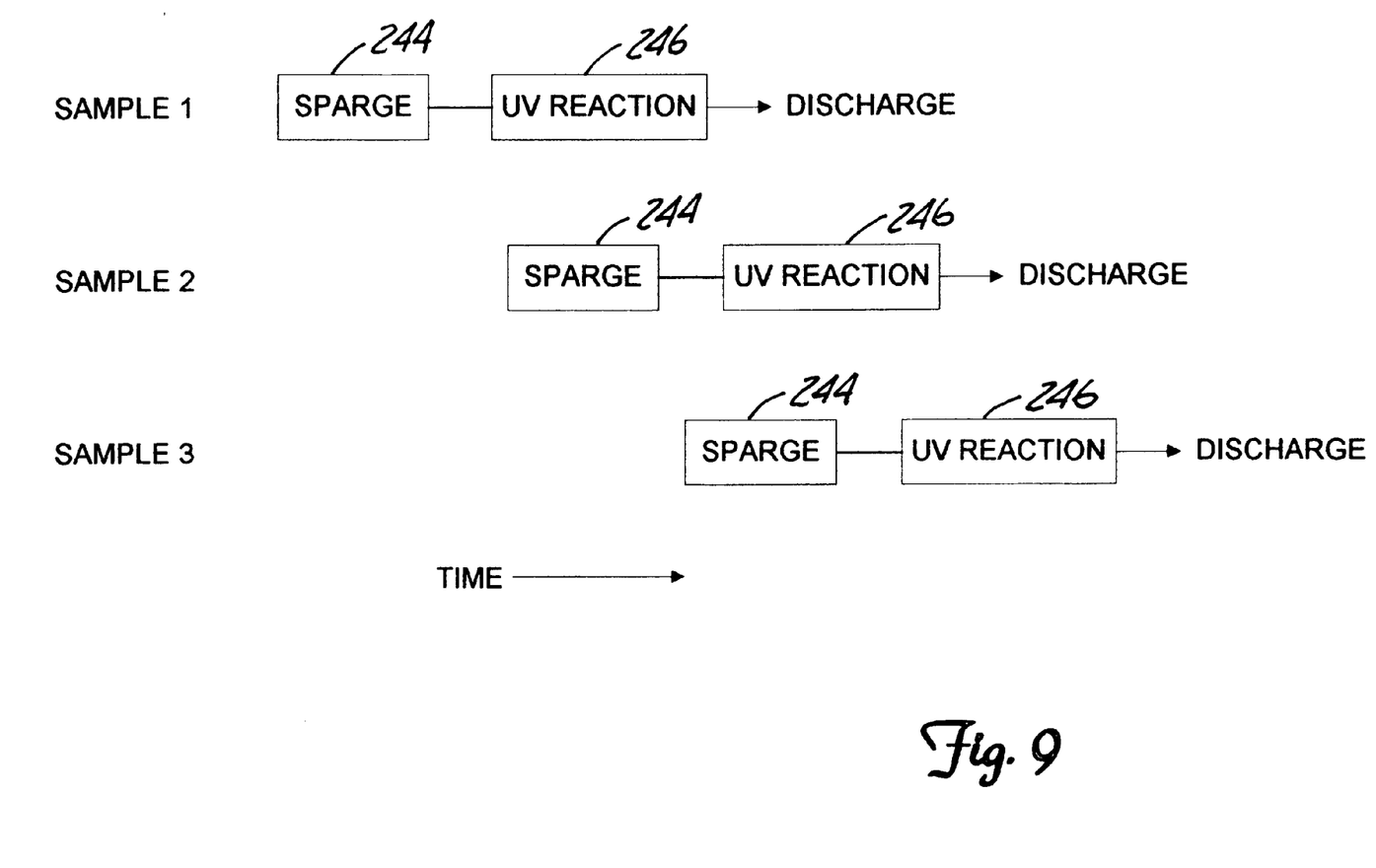
FIG. 9 depicts a method of measuring TOC on multiple samples.

It will be noted from FIG. 8 that the sparging chamber is substantially idle after block 226, where a volume $V_1$ of liquid is transferred to the UV chamber. This fact can be used to advantage when processing multiple samples. FIG. 9 depicts in simplified form a procedure based on FIG. 8 for processing multiple samples in a shortened overall time period. In FIG. 9, sparge blocks 244 represent a sparging chamber rinse procedure followed by blocks 210,212,214, 216,218 of FIG. 8. UV reaction blocks 246 represent block 220 through block 186 of FIG. 8. While one sample is being processed in UV chamber 30, the sparging chamber is rinsed and loaded with the next sample. Inorganic carbon is thus removed from the subsequent sample in the sparging chamber at the same time organic carbon in the prior sample is being converted to $CO_2$, removed from UV chamber 30, and detected by $CO_2$ detector 98. The time savings realized by the procedure of FIG. 9 are greatest where scores of samples are to be processed in sequence, such as with an autosampler.

TC Procedure

Figure 10:
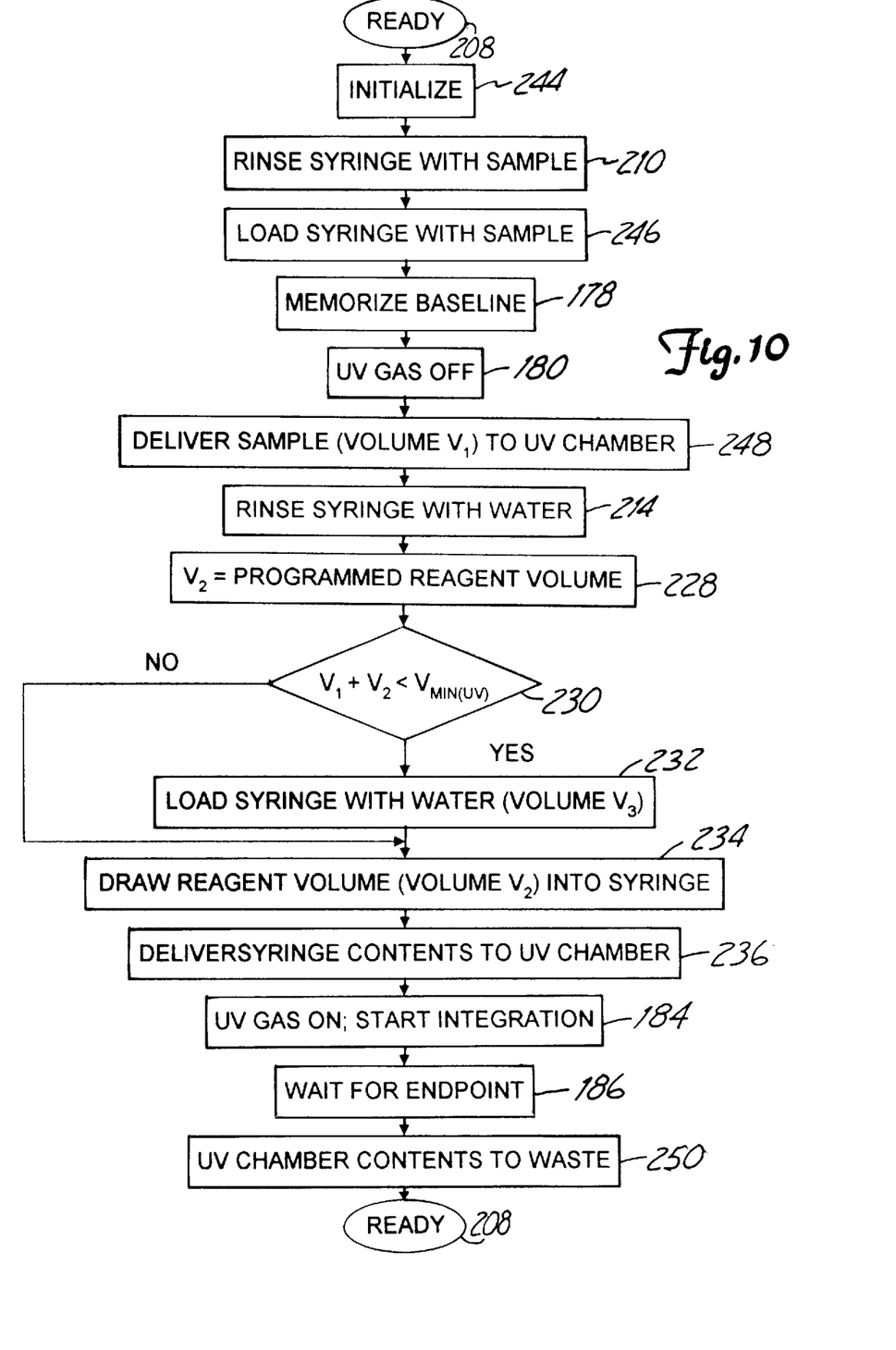
FIG. 10 is a flow chart of a preferred method of measuring TC.

Analyzer 12 can also be used to measure the TC content of a sample (see FIG. 10). In this procedure, acid and persulfate are added to the sample in the UV chamber, where both IC and TOC are converted to $CO_2$. The $CO_2$ is swept out of the UV chamber by the carrier gas and detected by the $CO_2$ detector.

In initialization block 244, valves 72,74,90,94 are set to off, on, on, on respectively. This shuts off carrier gas flow to the sparging chamber, turns on carrier gas flow to the UV chamber, and routes gas exiting the UV chamber to $CO_2$ detector 98. Sample is loaded into syringe 14 at block 246 after rinse step 210. Baseline is monitored (block 178) and UV chamber gas shut off (block 180), and then a volume $V_1$ of sample is delivered to the UV chamber at block 248. The remaining blocks of FIG. 10 have been described above, except for block 250 where the UV chamber contents are aspirated to the syringe pump and then discharged directly to waste.

IC Procedure

Figure 11:
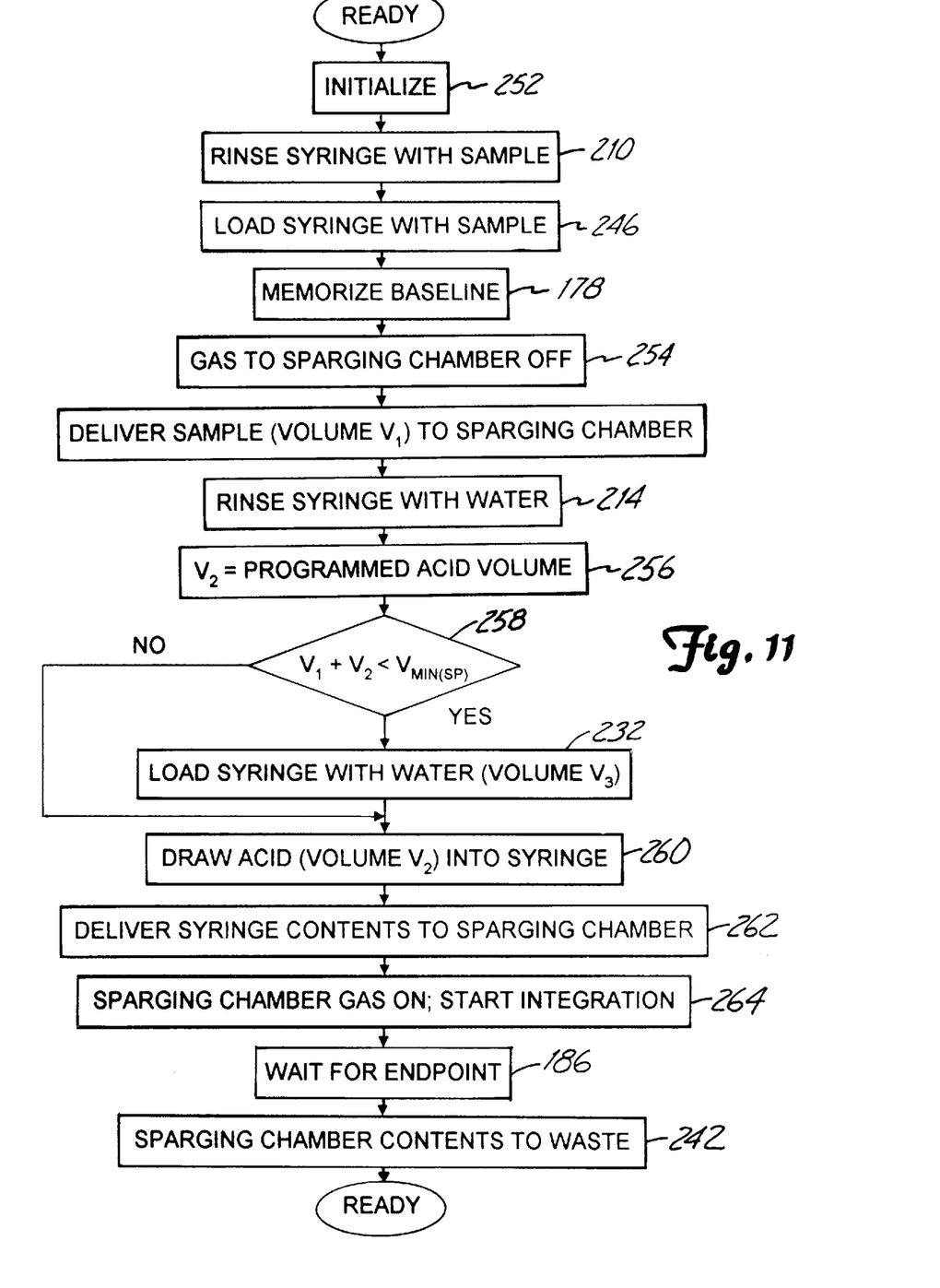
FIG. 11 is a flow chart of a preferred method of measuring IC.

Analyzer 12 can also measure the IC content of a sample as shown in FIG. 11. In this procedure, the sample is mixed with acid in the sparging chamber. Inorganic carbon in the sample reacts with the acid to form $CO_2$ gas, which is sparged out of the sample and carried to the $CO_2$ detector.

Referring to FIG. 11, from the ready state 208 the analyzer 12 is initialized at block 252. Valves 72,74,90,94 are set to on, off, off, off respectively. Carrier gas 60 does not flow through UV chamber 30 but does flow through sparging chamber 26 and from there to $CO_2$ detector 98. After blocks 210, 246, 178, a block 254 shuts off valve 72, turning off carrier gas flow to sparging chamber 26 to prepare for sample loading. Sample is then delivered (block 212) and the syringe rinsed (block 214). Block 256 is analogous to block 228 except $V_2$ is defined in FIG. 11 as the desired acid volume. Decision block 258 is similar to earlier decision block 230, except that $V_{min(SP)}$, a minimum recommended liquid volume for sparging chamber 26, is substituted for $V_{min(UV)}$. $V_{min(SP)}$ is selected such that the liquid in the sparging chamber covers a sufficient amount of sparge tube 84 for efficient sparging. If operation passes to block 232, the indicated volume $V_3$ is $V_{min(SP)}-(V_1+V_2)$. The preprogrammed volume $V_2$ of acid is added to the syringe at 260, and the contents ($V_2+V_3$, if any) of the syringe are added to the sample resident in the sparging chamber at block 262. Valve 72 is turned on and $CO_2$ detector integration immediately begins at 264. When integration is complete, a value representative of IC is obtained and operation passes from block 186 to blocks 242,208.

TOC (by Difference) Procedure

The amount of TOC in a sample can be rigorously measured by separately measuring the sample TC and IC. Sample TOC is then calculated as TOC=TC−IC.

Thus, the TC method of FIG. 10 is performed on a first aliquot of the sample, which first aliquot is then discharged to waste. A second aliquot of the sample is then taken, and analyzed according to the IC method of FIG. 11. The difference between the TC and IC values calculated by computer 112 then yields the sample TOC.

Although the present invention has been described with reference to preferred embodiments, workers skilled in the art will recognize that changes can be made in form and detail without departing from the spirit and scope of the invention.

What is claimed is:

1. An analytical instrument for measuring dissolved carbon in a liquid sample, comprising:
    a sample inlet;
    a reagent inlet;
    a rinse solution inlet;
    a UV reaction chamber;
    a sparging chamber;
    a waste outlet;
    a syringe pump; and
    a multiple port valve having a plurality of ports a,b,c,d,e and f, port a being coupled to the sample inlet, port b being coupled to the reagent inlet, port c being coupled to the rinse solution inlet, port d being coupled to the UV reaction chamber, port e being coupled to the sparging chamber, and port f being coupled to the waste outlet, the valve also including a primary port coupled to the syringe pump and selectively fluidically coupleable to each of the ports a–f to selectively fluidically couple a selected one of ports a–f to the syringe pump.

2. The analytical instrument of claim 1, further comprising:
    an acid inlet wherein the multiple port valve further includes a port g coupled to the acid inlet, the primary port being selectively fluidically coupleable to the port g to selectively fluidically couple port g to the syringe pump.

3. The analytical instrument of claim 1, wherein the multiple port valve includes two additional ports and comprises an 8-port valve.

4. The analytical instrument of claim 1 wherein the liquid sample is carried among the UV reaction chamber, the sparging chamber and the syringe pump along a liquid travel path, and wherein the multiple port valve is substantially the sole valve in the liquid travel path.

5. The analytical instrument of claim 1, wherein the syringe pump has a capacity of at least 10 milliliters.

6. The analytical instrument of claim 1 wherein at least one of ports a–f comprises an upward facing port that faces at least partially upward relative to a horizontal plane.

7. The analytical instrument of claim 6 wherein at least one of ports b and c is an upward facing port.

8. The analytical instrument of claim 6 wherein at least one of ports a and f comprises a downward facing port, facing downward relative to the horizontal plane.

9. The analytical instrument of claim 6 wherein port d is between port a and at least one of ports b and c.

10. The analytical instrument of claim 9 wherein port a is adjacent to at least one of ports d and e.

11. An analytical instrument for measuring carbon in a sample, comprising:
   a UV reaction chamber having a sparge tube, the chamber adapted to hold the sample and convert carbon in the sample to $CO_2$;
   a syringe pump to deliver the sample to the UV reaction chamber and to remove the sample from the UV reaction chamber after carbon in the sample is converted to $CO_2$;
   a detector to measure $CO_2$ from the UV reaction chamber; and
   wherein the UV reaction chamber includes a vessel having a port at the bottom thereof for the delivery and removal of the sample, and a UV lamp disposed in the vessel and having a spiral configuration, wherein the sparge tube extends into the UV lamp.

12. The analytical instrument of claim 11, wherein the port is the sole aperture in the vessel that carries liquids to or from the UV reaction chamber.

13. The analytical instrument of claim 11, further comprising:
   a reagent inlet;
   wherein the syringe pump further is configured to receive a reagent from the reagent inlet and deliver the reagent to the UV reaction chamber.

14. An analytical instrument for measuring carbon in a sample, comprising:
   a UV reaction chamber to hold the sample and convert carbon in the sample to $CO_2$;
   a syringe pump to deliver the sample to the UV reaction chamber and to remove the sample from the UV reaction chamber after carbon in the sample is converted to $CO_2$;
   a detector to measure $CO_2$ from the UV reaction chamber; and
   wherein the UV reaction chamber includes a vessel having a port at the bottom thereof for the delivery and removal of the sample, and a UV lamp disposed in the vessel and having a spiral configuration, the UV lamp including a tube having a tube diameter and shaped into a plurality of coils, the coils being spaced apart by a gap no greater than the tube diameter.

15. An analytical instrument for measuring carbon in a sample, comprising:
   a UV reaction chamber to hold the sample and convert carbon in the sample to $CO_2$;
   a syringe pump to deliver the sample to the UV reaction chamber and to remove the sample from the UV reaction chamber after carbon in the sample is converted to $CO_2$; and
   a detector to measure $CO_2$ from the UV reaction chamber;
   wherein the UV reaction chamber includes a vessel having an open upper end and a port at the bottom thereof for the delivery and removal of the sample, and a UV lamp disposed in the vessel and having a spiral configuration;
   wherein the chamber further includes a cap threadingly mating with the open upper end of the vessel.

* * * * *